United States Patent

Scott et al.

[11] Patent Number: 5,763,704
[45] Date of Patent: Jun. 9, 1998

[54] PRODUCTION OF DIFLUOROMETHANE

[75] Inventors: John David Scott, Cheshire; Michael John Watson, Chester; David William Bonniface, Kingsley, all of United Kingdom

[73] Assignee: Imperial Chemical Industries PLC, United Kingdom

[21] Appl. No.: 522,241

[22] PCT Filed: Mar. 14, 1994

[86] PCT No.: PCT/GB94/00498

§ 371 Date: Sep. 6, 1995

§ 102(e) Date: Sep. 6, 1995

[87] PCT Pub. No.: WO94/21580

PCT Pub. Date: Sep. 29, 1994

[30] Foreign Application Priority Data

Mar. 24, 1993 [GB] United Kingdom .......... 9306072
Mar. 24, 1993 [GB] United Kingdom .......... 9306089

[51] Int. Cl.⁶ .......................................... C07C 17/08
[52] U.S. Cl. .......................... 570/165; 570/168; 570/169
[58] Field of Search ............................. 570/165, 168, 570/169

[56] References Cited

FOREIGN PATENT DOCUMENTS

| | | |
|---|---|---|
| A 0 128 510 | 12/1984 | European Pat. Off. |
| A 0 502 605 | 9/1992 | European Pat. Off. |
| WO A 92/16482 | 10/1992 | WIPO . |

*Primary Examiner*—Alan Siegel

[57] ABSTRACT

There is provided a process for the production of difluoromethane which comprises contacting a dichloromethane with hydrogen fluoride in the presence of a fluorination catalyst comprising zinc or a compound of zinc and metal oxide, fluoride or oxyfluoride.

8 Claims, No Drawings

PRODUCTION OF DIFLUOROMETHANE

This application is a 371 of PCT/GB94/00498 filed Mar. 14, 1994.

This invention relates to a process for the production of difluoromethane.

In recent years there has been increasing international concern that chlorofluorocarbons, which are used on a large scale around the world, may be damaging the earth's protective ozone layer and there is now in place international legislation to ensure that their manufacture and use is completely phased out. Chlorofluorocarbons are used, for example, as refrigerants, as foam blowing agents, as cleaning solvents and as propellants for aerosol sprays in which the variety of applications is virtually unlimited. Consequently, much effort is being devoted to finding suitable replacements for chlorofluorocarbons which will perform satisfactorily in the many applications in which chlorofluorocarbons are used but which will not have the aforementioned damaging effect on the ozone layer. One approach in the search for suitable replacements has centred on fluorocarbons which do not contain chlorine but which contain hydrogen. The hydrofluorocarbon difluoromethane, also known as HFA 32, is of interest as one such replacement, in particular in a blend thereof with other hydrofluoroalkanes, for example HFA 134a and HFA 125, as a replacement for R-22 and R-502 in refrigeration, air-conditioning and other applications.

Processes have been proposed for the production of difluoromethane. Thus, in U.S. Pat. No. 2,744,148, there is described a process for the production of difluoromethane comprising contacting dichloromethane with hydrogen fluoride in the presence of a fluorination catalyst which comprises nickel, chromium, cobalt, copper or palladium carried on aluminium fluoride. Many other catalysts have been proposed for use in the hydrofluorination of dichloromethane, for example, chromium fluoride on alumina in U.S. Pat. No. 4,147733; aluminium fluoride, chromium fluoride, mixtures thereof, aluminium fluoride on active carbon or ferric chloride on active carbon in EP 128510; chromium oxyfluoride in U.S. Pat. No. 2,745,886 and chromia in GB 1,307,224.

However, a serious problem with the production of difluoromethane by the hydrofluorination of dichloromethane is that a substantial amount of a highly toxic by-product, monochloromonofluoromethane, HCFC 31, is produced as an intermediate. HCFC 31 has an Occupational Exposure Limit of 10 parts per billion, and may be produced in substantial quantities, indeed as much as 20% or more of the product from the hydrofluorination of dichloromethane.

We have now found that with certain fluorination 1 catalysts the selectivity to difluoromethane may be substantially increased and thus the yield of HCFC 31 produced may be substantially decreased.

According to the present invention there is provided a process for the production of difluoromethane comprising contacting dichloromethane with hydrogen fluoride in the presence of a fluorination catalyst comprising zinc or a compound of zinc and a metal oxide, fluoride or oxyfluoride.

We prefer to employ a catalyst as described in EP 0502605 or PCT/GB93/00244, the disclosures of which are incorporated herein by reference.

Thus the metal of the metal oxide, fluoride or oxyfluoride, the amount of zinc, the catalyst preparation method, the catalyst prefluorination treatment, the form of the catalyst, the catalyst regeneration treatment, and the presence of other metals or compounds thereof in the catalyst may be as described in EP 0502605 or PCT/GB93/00244, and especially as described in EP 0502605. These preferred catalyst preparations, forms and compositions are disclosed in this document as they are described in EP 0502605 and PCT/GB93/00244.

The conditions of temperature, pressure and amount of starting materials under which the process is carried out may be as previously proposed for the hydrofluorination of dichloromethane. Thus, the temperature may be in the range from about 100° C. to about 500° C., preferably from about 200° C. to about 400° C., although use of the catalyst of the present invention generally allows lower temperatures to be used than those employed in the prior art whilst the level of HCFC 31 produced may not be increased compared with the levels of HCFC 31 produced at higher temperatures using catalysts previously proposed. The use of lower temperatures results in substantially longer catalyst lifetimes with a consequent reduction in the frequency with which the catalyst requires regeneration. The temperature is especially preferably in the range from about 170° C. to about 340° C. and particularly in the range from about 240° C. to about 320° C.

The process may be operated at about atmospheric pressure although superatmospheric or subatmospheric pressure may be employed if desired. Superatmospheric pressures, say up to about 30 bar, are conveniently employed.

Typically a stoichiometric excess of hydrogen fluoride to dichloromethane is employed, and the molar ratio of hydrogen fluoride to dichloromethane 1 will usually be at least about 3:1, preferably at least 5:1, and less than 100:1, preferably less than about 50:1. Molar ratios of hydrogen fluoride to dichloromethane in the range from about 5:1 to about 25:1 are especially preferred.

Difluoromethane is conveniently separated from unreacted starting materials and intermediate HCFC 31 by conventional techniques, for example distillation and the process is preferably operated on a continuous basis in which unreacted starting materials and HCFC 31 are recycled.

The invention is illustrated but not limited by the following examples.

EXAMPLE 1

1 g of a zinc/chromium mixed oxide catalyst prepared by co-precipitation and comprising 8% by weight zinc was charged to a ½" diameter Inconel reactor tube and heated to 300° C. in nitrogen. Hydrogen fluoride was then passed over the catalyst for 24 hours at 300° C. and the reactor was then cooled to 250° C.

The reactor was pressurised to 10 bar in nitrogen and dichloromethane and hydrogen fluoride were passed over the catalyst in the mole ratios indicated in Table 1. The vent gas from the reactor was scrubbed with water to remove hydrogen fluoride and hydrogen chloride, sampled and analysed by Gas Chromatography. The results are shown in Table 1.

TABLE 1

| HF:CH$_2$Cl$_2$ | Off Gas Composition (% v/v) | | |
|---|---|---|---|
| (Mole ratio) | CH$_2$Cl$_2$ | CH$_2$ClF | CH$_2$F$_2$ |
| 27.1 | 1.0 | 7.1 | 92.0 |
| 21.3 | 2.3 | 10.0 | 87.7 |
| 19.6 | 2.8 | 11.1 | 86.1 |
| 12.5 | 7.4 | 9.4 | 83.1 |
| 11.2 | 6.4 | 8.9 | 84.7 |
| 11.5 | 5.4 | 8.2 | 86.4 |
| 12.2 | 5.8 | 8.4 | 85.7 |

EXAMPLE 2

The procedure of Example 1 was repeated except that atmospheric pressure was employed and the temperature was as shown in Table 2 below in which the results are also shown.

TABLE 2

| HF:CH$_2$Cl$_2$ | Temp | Off Gas Composition (% v/v) | | |
|---|---|---|---|---|
| (Mole ratio) | (°C.) | CH$_2$Cl$_2$ | CH$_2$ClF | CH$_2$F$_2$ |
| 7.0 | 210 | 35.0 | 12.1 | 52.9 |
| 7.1 | 230 | 20.8 | 10.9 | 68.3 |
| 6.3 | 250 | 17.1 | 11.1 | 71.9 |
| 15.9 | 250 | 3.5 | 5.2 | 91.3 |
| 16.1 | 200 | 34.7 | 11.3 | 54.0 |

EXAMPLE 3

The procedure of Example 2 was repeated except that the catalyst comprised 2% w/w zinc on alumina prepared by impregnating gamma alumina having an initial surface area of 180 m$^2$/g with an aqueous solution of zinc chloride. The conditions and results are shown in Table 3 below.

TABLE 3

| HF:CH$_2$Cl$_2$ | Temp | Off Gas Composition (% v/v) | | |
|---|---|---|---|---|
| (Mole ratio) | (°C.) | CH$_2$Cl$_2$ | CH$_2$ClF | CH$_2$F$_2$ |
| 16.0 | 200 | 61.4 | 15.4 | 23.2 |
| 16.9 | 200 | 64.1 | 15.6 | 20.3 |

We claim:

1. A process for the production of difluoromethane comprising contacting dichloromethane with hydrogen fluoride in the presence of a fluorination catalyst comprising zinc or a compound of zinc and a metal oxide, fluoride or oxyfluoride.

2. A process as claimed in claim 1 in which the catalyst comprises zinc or a compound of zinc and chromia, chromium fluoride or chromium oxyfluoride.

3. A process as claimed in claim 1 wherein the contacting is carried out at a temperature of from about 170° C. to about 340° C.

4. A process as claimed in claim 1 or claim 2 in which the molar ratio of hydrogen fluoride to dichloromethane is in the range from about 5:1 to about 25:1.

5. A process as claimed in claim 1 in which the weight % of zinc based on the weight of the catalyst is in the range from about 0.5% to about 30%.

6. A process as claimed in claim 3 in which the temperature is in the range from about 240° to about 320° C.

7. A process as claimed in claim 1 in which the molar ratio of hydrogen fluoride to dichloromethane is in the range from about 3:1 to less than 100:1.

8. A process as claimed in claim 1 in which an amount of monochloromonofluoromethane produced is substantially reduced.

* * * * *